United States Patent
Tomatsu et al.

(10) Patent No.: US 9,833,127 B2
(45) Date of Patent: Dec. 5, 2017

(54) WIRE CONNECTION DEVICE, CAMERA HEAD AND ENDOSCOPIC DEVICE

(71) Applicants: SONY OLYMPUS MEDICAL SOLUTIONS INC., Tokyo (JP); SONY CORPORATION, Tokyo (JP)

(72) Inventors: Kei Tomatsu, Tokyo (JP); Taichi Hirano, Tokyo (JP); Akira Matsuda, Tokyo (JP)

(73) Assignees: SONY OLYMPUS MEDICAL SOLUTIONS INC., Tokyo (JP); SONY CORPORATION, Tokyo (JP)

(*) Notice: Subject to any disclaimer, the term of this patent is extended or adjusted under 35 U.S.C. 154(b) by 223 days.

(21) Appl. No.: 14/628,818

(22) Filed: Feb. 23, 2015

(65) Prior Publication Data

US 2015/0250378 A1 Sep. 10, 2015

(30) Foreign Application Priority Data

Mar. 4, 2014 (JP) .................................. 2014-042086
Dec. 4, 2014 (JP) .................................. 2014-246063

(51) Int. Cl.
*H01R 13/64* (2006.01)
*A61B 1/00* (2006.01)
*H04N 7/10* (2006.01)
*H04N 5/225* (2006.01)
(Continued)

(52) U.S. Cl.
CPC .......... *A61B 1/00124* (2013.01); *A61B 1/042* (2013.01); *H01R 13/6471* (2013.01); *H04N 5/2251* (2013.01); *H04N 7/102* (2013.01); *H04N 2005/2255* (2013.01)

(58) Field of Classification Search
None
See application file for complete search history.

(56) References Cited

U.S. PATENT DOCUMENTS 7,448,884 B2 * 11/2008 Kato .................. H01R 23/6873
439/108
2002/0039857 A1 * 4/2002 Naito ................ H01R 23/6873
439/493
(Continued)

FOREIGN PATENT DOCUMENTS

| JP | 2008-41656 A | 2/2008 |
| JP | 2010-287560 A | 12/2010 |
| JP | 2012-226903 A | 11/2012 |

*Primary Examiner* — Reza Aghevli
(74) *Attorney, Agent, or Firm* — Oblon, McClelland, Maier & Neustadt, L.L.P.

(57) ABSTRACT

There is provided a wire connection device including an outer frame that has a tubular shape, and a plurality of contacts that are provided in the outer frame, and that have a plurality of pairs of differential contacts to which a plurality of pairs of differential signals are respectively allocated, and a plurality of ground contacts each to which ground is allocated. When viewed from a direction along a central axis of the outer frame, the plurality of contacts are arranged side by side in two rows in a manner that the differential contacts of each pair can be adjacent to each other and in a manner that the number of the ground contacts adjacent to one of the differential contacts of each pair is equal to the number of the ground contacts adjacent to the other one of the differential contacts of the pair.

14 Claims, 13 Drawing Sheets

(51) Int. Cl.
*H01R 13/6471* (2011.01)
*A61B 1/04* (2006.01)

(56) References Cited

U.S. PATENT DOCUMENTS

| | | | |
|---|---|---|---|
| 2004/0067680 A1* | 4/2004 | Wu | H01R 13/6589 439/497 |
| 2011/0053430 A1* | 3/2011 | Bopp | H01R 13/6658 439/676 |
| 2014/0041937 A1* | 2/2014 | Lloyd | H01B 11/00 174/74 R |
| 2016/0028189 A1* | 1/2016 | Resendez | H01R 9/034 439/607.01 |
| 2016/0268739 A1* | 9/2016 | Zerebilov | H01R 24/60 |

* cited by examiner

WIRE CONNECTION DEVICE, CAMERA HEAD AND ENDOSCOPIC DEVICE

CROSS REFERENCE TO RELATED APPLICATIONS

This application claims the benefit of Japanese Priority Patent Application JP 2014-042086 filed Mar. 4, 2014, and Japanese Priority Patent Application JP 2014-246063 filed Dec. 4, 2014, the entire contents of each of which are incorporated herein by reference.

BACKGROUND

The present disclosure relates to wire connection device, a camera head and an endoscopic device.

In the past, there has been known a connector mechanically and electrically connected to a counterpart connector, such as a plug and a receptacle (see JP2010-287560A, for example).

The connector described in JP2010-287560A includes multiple contacts arranged side by side in a row. The multiple contacts include multiple pairs of differential contacts and multiple ground contacts. To the multiple pairs of differential contacts, multiple pairs of differential signals are respectively allocated. Each of the multiple ground contacts, to which ground is allocated, is placed between a pair of differential contacts and another pair of differential contacts.

Thus, in the connector described in JP2010-287560A, crosstalk is prevented by placing each ground contact at the position.

SUMMARY

However, the connector described in JP2010-287560A has a problem of difficulty in downsizing since the arrangement of multiple contacts arranged side by side in a row increases width dimension in the side-by-side arrangement direction.

The present disclosure is made in view of the above. According to embodiments of the present disclosure, there is provided a wire connection device, a camera head and an endoscopic device which are capable of preventing signal deterioration while achieving downsizing.

According to an embodiment of the present disclosure, there is provided a wire connection device including an outer frame that has a tubular shape, and a plurality of contacts that are provided in the outer frame, and that have a plurality of pairs of differential contacts to which a plurality of pairs of differential signals are respectively allocated, and a plurality of ground contacts each to which ground is allocated. When viewed from a direction along a central axis of the outer frame, the plurality of contacts are arranged side by side in two rows in a manner that the differential contacts of each pair can be adjacent to each other and in a manner that the number of the ground contacts adjacent to one of the differential contacts of each pair is equal to the number of the ground contacts adjacent to the other one of the differential contacts of the pair.

According to an embodiment of the present disclosure, when viewed from the direction along the central axis of the outer frame, the plurality of contacts may be arranged so as to constitute part of an equilateral triangular lattice where intervals of mutually adjacent lattice points are identical.

According to an embodiment of the present disclosure, the plurality of pairs of differential contacts may be arranged in a manner that one of the differential contacts of each pair is arranged in a first row of the two rows while the other one of the differential contacts of the pair is arranged in a second row of the two rows.

According to an embodiment of the present disclosure, the plurality of pairs of differential contacts may be arranged in a manner that both the differential contacts of each pair are arranged in either of a first row and a second row of the two rows.

According to an embodiment of the present disclosure, when viewed from the direction along the central axis of the outer frame, each of the plurality of contacts may be formed of a female contact including a first contact portion that has an L shape and that has a first sidewall portion extending in a side-by-side arrangement direction of either of a first row and a second row of the two rows, and a second sidewall portion crossing the first sidewall portion. The plurality of contacts may be arranged in a manner that separation distances between each two of the second sidewall portions mutually adjacent in the side-by-side arrangement direction are identical.

According to an embodiment of the present disclosure, each of the plurality of contacts may be formed of a female contact including a second contact portion that has a plate shape extending in a side-by-side arrangement direction of either of a first row and a second row of the two rows.

According to an embodiment of the present disclosure, when viewed from the direction along the central axis of the outer frame, each of the plurality of contacts may be formed of a female contact including a third contact portion that has a U shape and that has a base portion extending in a side-by-side arrangement direction of either of a first row and a second row of the two rows, and a pair of third sidewall portions erecting from the base portion and facing to each other in the side-by-side arrangement direction.

According to an embodiment of the present disclosure, the plurality of pairs of differential contacts may be arranged in a manner that one of the differential contacts of each pair is arranged in the first row while the other one of the differential contacts of the pair is arranged in the second row. The one differential contact and the other differential contact may be arranged symmetrically with respect to a point positioned at a center between the one differential contact and the other differential contact.

According to an embodiment of the present disclosure, when viewed from the direction along the central axis of the outer frame, the plurality of contacts may be arranged in a manner that the number of the ground contacts adjacent to one of the differential contacts of each pair and the number of the ground contacts adjacent to the other one of the differential contacts of the pair are set to one.

According to an embodiment of the present disclosure, there is provided a camera head used in an endoscope, the camera head including the wire connection device, and an image sensor electrically connected to the plurality of contacts.

According to an embodiment of the present disclosure, the wire connection device may be formed of two connectors mechanically and electrically connected to each other, the connectors being a first connector and a second connector.

According to an embodiment of the present disclosure, there is provided an endoscopic device including the camera head.

In the wire connection device according to an embodiment of the present disclosure, the multiple contacts are arranged side by side in two rows when viewed from the direction along the central axis of the outer frame. Thus, an increase in width dimension in the side-by-side arrangement direction can be avoided as compared to a wire connection device (the connector described in JP2010-287560A, for example) in which multiple contacts are arranged side by side in a row.

Furthermore, in the wire connection device according to an embodiment of the present disclosure, the multiple contacts are arranged so that the differential contacts of each pair can be adjacent to each other and so that the number of the ground contacts adjacent to one of the differential contacts of each pair can be equal to the number of the ground contacts adjacent to the other one of the differential contacts of the pair. Thus, the number of so-called ground guards for each differential signal can be fixed, and consequently signal deterioration can be prevented.

Therefore, the wire connection device according to an embodiment of the present disclosure has an effect of preventing signal deterioration while achieving downsizing.

The camera head according to an embodiment of the present disclosure includes the wire connection device, thus having a similar effect.

The endoscopic device according to an embodiment of the present disclosure includes the camera head, thus having a similar effect.

DETAILED DESCRIPTION OF THE EMBODIMENT

Figure 1:
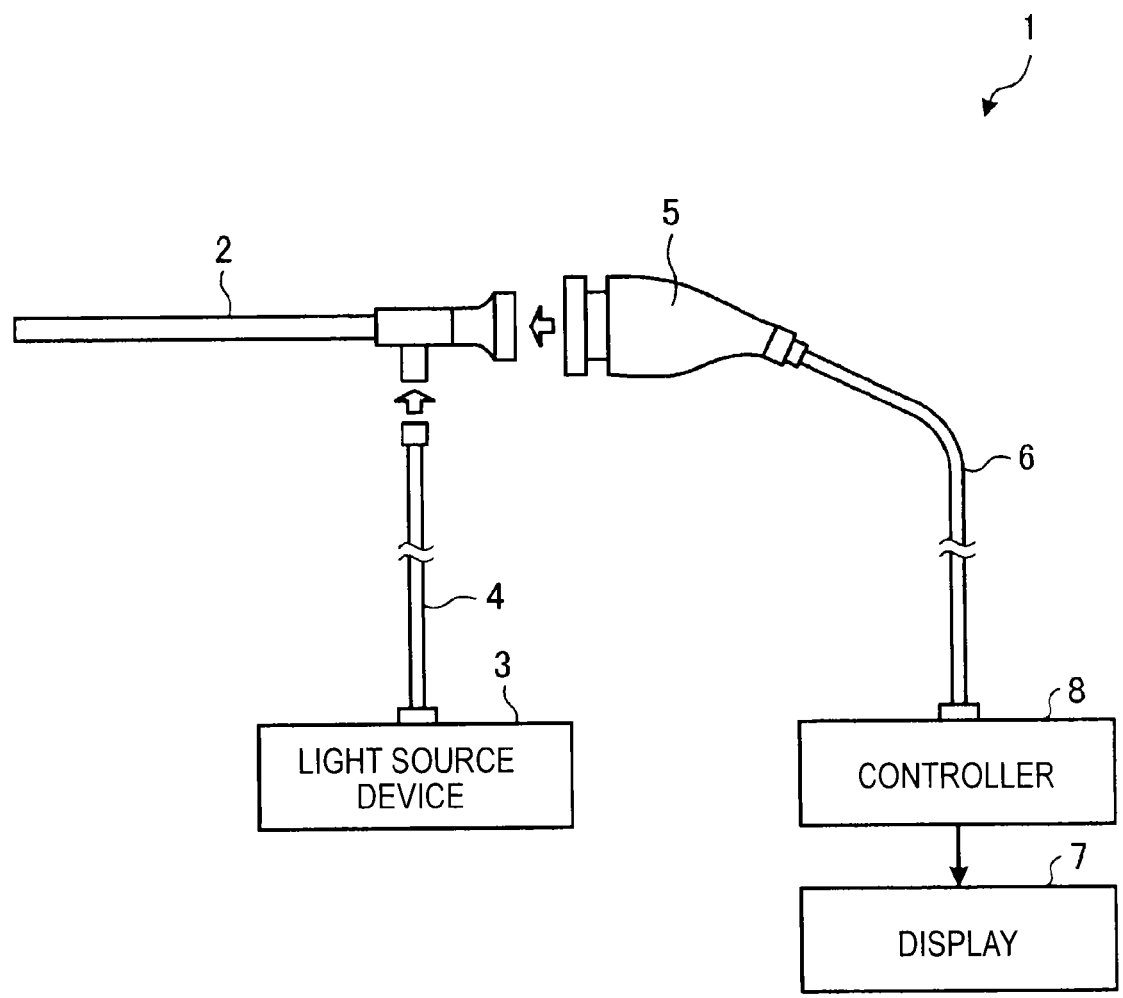
FIG. 1 shows a schematic configuration of an endoscopic device according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

[Schematic Configuration of Endoscopic Device]

FIG. 1 shows a schematic configuration of an endoscopic device 1 according to an embodiment of the present disclosure. The endoscopic device 1 is an apparatus used in medical fields to observe the interior of an observation object (interior of a living body) such as a human being. Note that, though an endoscopic device using a rigid scope (insertion part 2) will be described as the endoscopic device 1 in this embodiment, the endoscopic device 1 is not limited thereto, but may be an endoscopic device using a flexible scope (not shown). As shown in FIG. 1, the endoscopic device 1 includes the insertion part 2, a light source device 3, a light guide 4, a camera head 5, a composite cable 6, a display 7 and a controller 8.

The insertion part 2, being rigid and having an elongated shape, is inserted into an observation object. An optical system for condensing light to form an object image is provided inside the insertion part 2.

The light source device 3 is connected to one end of the light guide 4, and supplies the one end of the light guide 4 with light to illuminate the interior of the observation object.

While the one end of the light guide 4 is detachably connected to the light source device 3, the other end is detachably connected to the insertion part 2. The light guide 4 transmits light supplied from the light source device 3 from the one end to the other end, thereby supplying the light to the insertion part 2. The light supplied to the insertion part 2 is emitted from the distal end of the insertion part 2, and thereby the interior of the observation object is irradiated with the light. The light (object image) with which the interior of the observation object is irradiated is condensed by the optical system in the insertion part 2.

The camera head 5 is detachably connected to the base end of the insertion part 2. Under control of the controller 8, the camera head 5 images the object image formed with light condensed by the insertion part 2, then photoelectrically converts imaging signals (electrical signals) obtained by the imaging into optical signals, and outputs the optical signals.

In this embodiment, a differential transmission system is employed. Accordingly, information (imaging signals (electrical signals and optical signals)) obtained by imaging by the camera head 5 is transmitted to the controller 8 through the composite cable 6 as multiple pairs of differential signals (+) and differential signals (−). Here, the differential signal (+) and the differential signal (−) of each pair are signals having mutually opposite phases.

The detailed configuration of the camera head 5 will be described later.

The composite cable 6 has multiple optical fibers 61 (see FIG. 7) and multiple electrical signal cables 62 (see FIG. 7) inside a jacket 6A (see FIG. 7), which is the outermost layer. One end of the composite cable 6 is detachably connected to the controller 8 while the other end is detachably connected to the camera head 5.

The multiple optical fibers 61 are arranged at a center position of the composite cable 6 in a cross sectional view of the composite cable 6, and used for transmitting optical signals between the camera head 5 and the controller 8.

The multiple electrical signal cables 62 are arranged around the multiple optical fibers 61 in a cross sectional view of the composite cable 6, and used for transmitting electrical signals between the camera head 5 and the controller 8.

The display 7 displays an image under control of the controller 8.

The controller 8 acquires optical signals (differential signals (+) and differential signals (−)) outputted from the camera head 5 through the multiple optical fibers 61, and photoelectrically converts the optical signals to electrical signals. Then, the controller 8 performs predetermined processing on the photoelectrically converted electrical signals, thereby causing the display 7 to display an image imaged by the camera head 5. Meanwhile, the controller 8 outputs control signals and the like (electrical signals) to the camera head 5 through the multiple electrical signal cables 62.

[Configuration of Camera Head]

Figure 2:
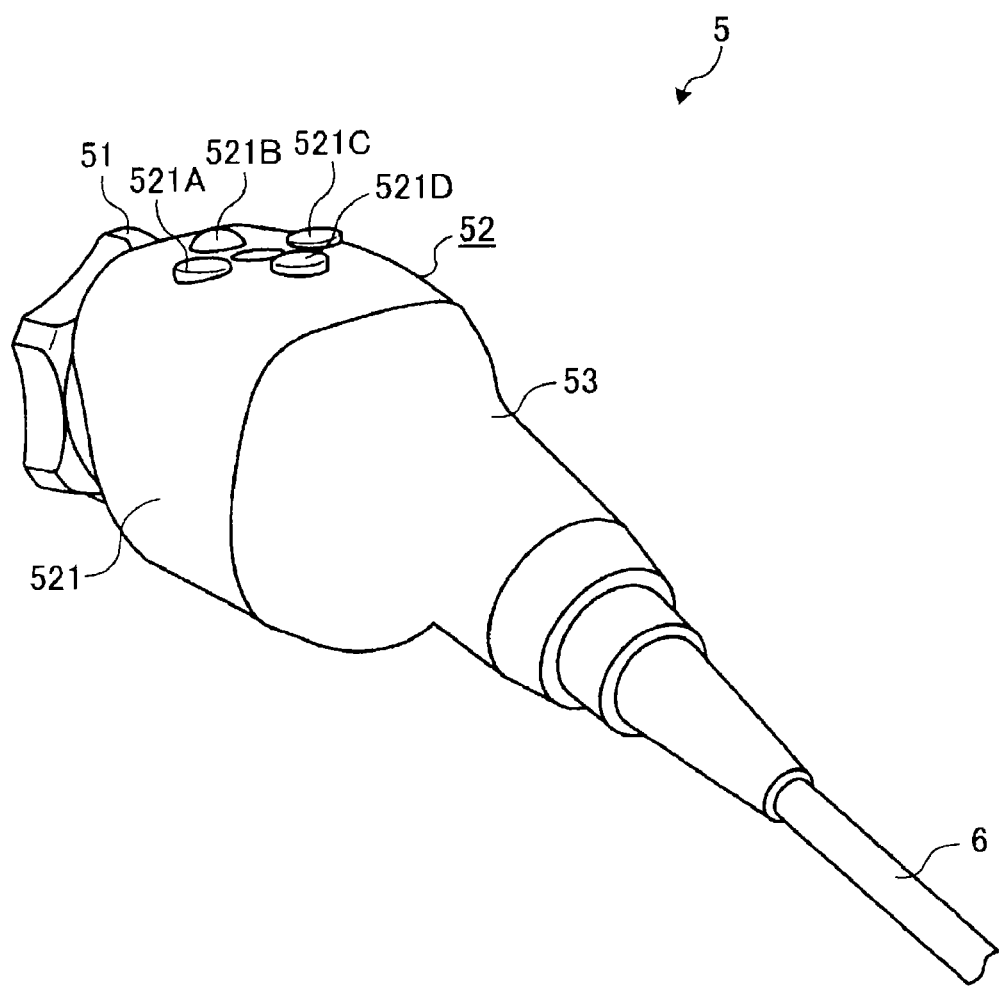
FIG. 2 is a perspective view, as viewed from the base-end side (side to which a composite cable is connected), of a camera head shown in FIG. 1.

FIG. 2 is a perspective view, as viewed from the base-end side (side to which the composite cable 6 is connected), of the camera head 5.

Figure 6:
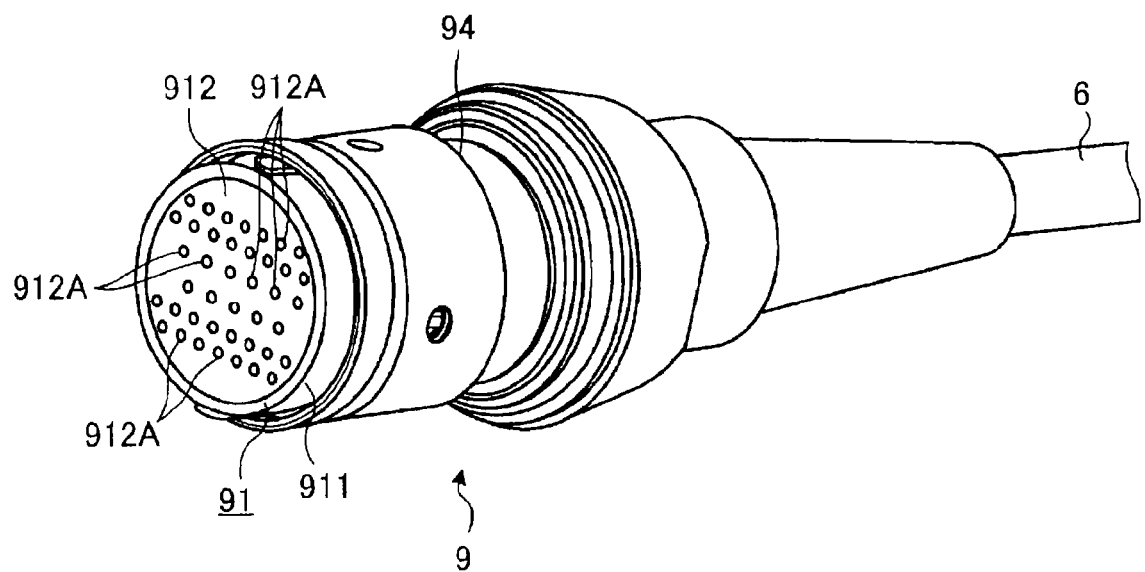
FIG. 6 is a perspective view, as viewed from the front-end side (side to which the airtight part is connected), of the photoelectric composite module according to an embodiment of the present disclosure.

As shown in FIG. 2, the camera head 5 includes a coupler part 51, an airtight part 52 and a photoelectric composite module 9 (see FIG. 6).

Note that FIG. 2 shows the state where a cover part 53, having a tubular shape to cover the photoelectric composite module 9 and the base-end side of the airtight part 52, is attached, thus not showing the photoelectric composite module 9.

The coupler part 51 is used for detachably connecting the camera head 5 to the base end of the insertion part 2, and provided at the front end of the camera head 5.

Figure 3:
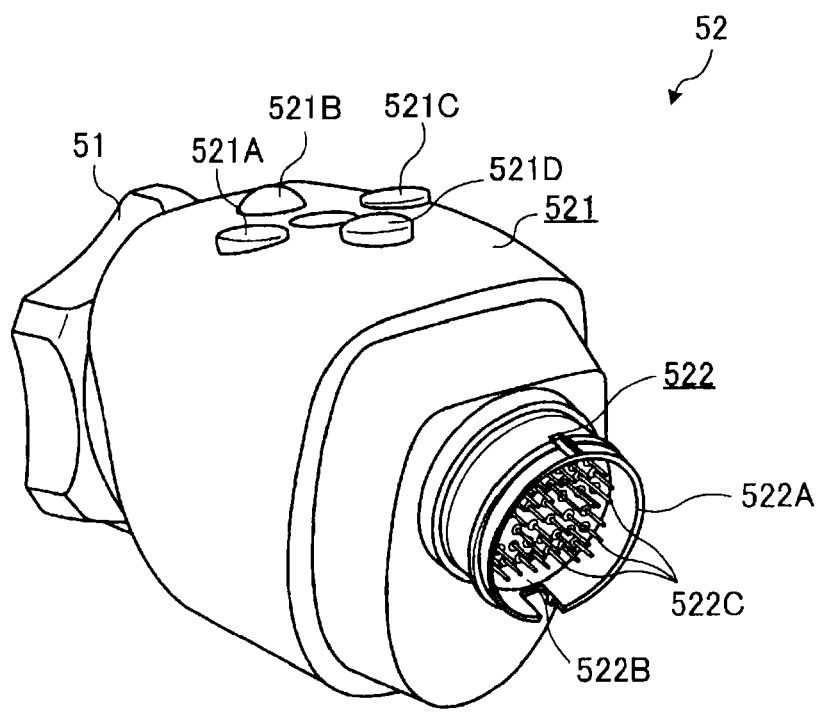
FIG. 3 is a perspective view, as viewed from the base-end side (side to which a photoelectric composite module is connected), of an airtight part shown in FIG. 2.

FIG. 3 is a perspective view, as viewed from the base-end side (side to which the photoelectric composite module 9 is connected), of the airtight part 52.

Figure 4:
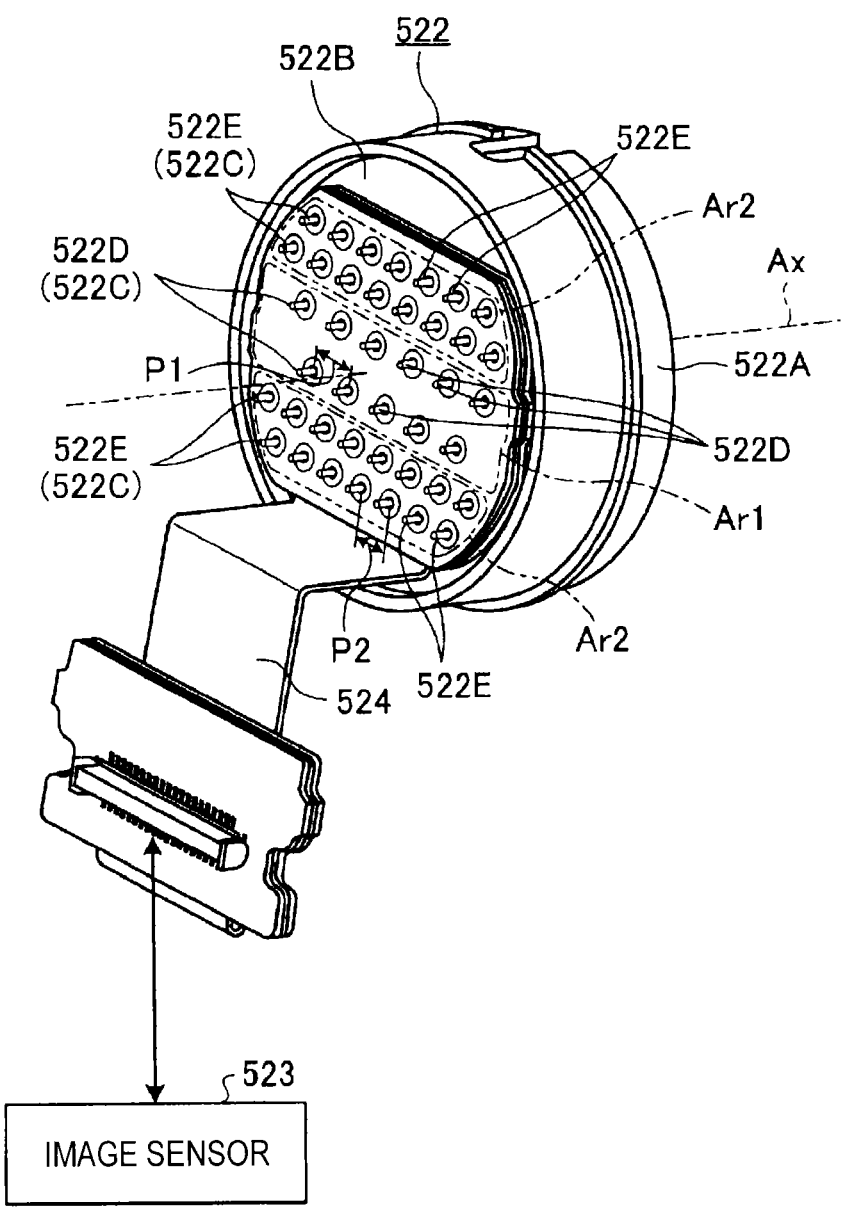
FIG. 4 is a perspective view, as viewed from the inside of the airtight part, of a hermetic connector shown in FIG. 3.

As shown in FIGS. 2 and 3, the airtight part 52 includes a casing 521 constituting the exterior of the airtight part 52, a hermetic connector 522 (FIG. 3) mounted on the casing 521, and parts housed in the casing 521 such as a lens unit (not shown), a driving motor (not shown) and an image sensor 523 (see FIG. 4).

The lens unit forms an object image with light condensed by the insertion part 2 onto an imaging surface of the image sensor 523. The lens unit is movable in the optical axis direction.

The driving motor moves the lens unit along the optical axis when any of switches 521A to 521D (FIGS. 2 and 3), provided to be exposed on the outer surface of the casing 521, is pressed, thereby adjusting a focal distance and a focus of the lens unit.

The image sensor 523 includes a charge coupled device (CCD) or a complementary metal oxide semiconductor (CMOS), a signal processing unit and the like. The CCD or CMOS receives light condensed by the lens unit and converts the light into the electrical signals. The signal processing unit performs signal processing on the electrical signals outputted by the CCD or CMOS, and outputs multiple pairs of differential signals (+) and differential signals (−).

Figure 5:
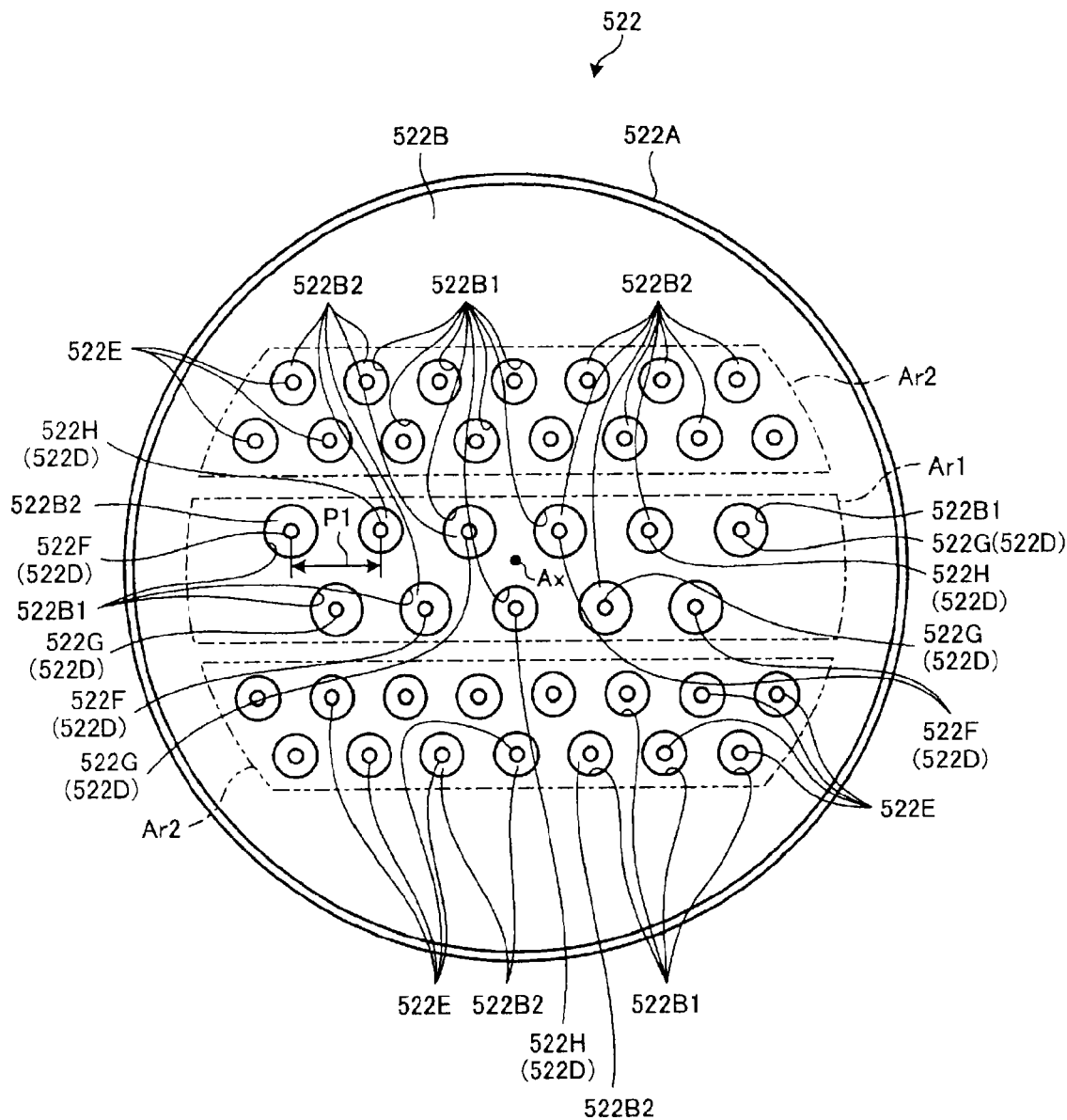
FIG. 5 is a view, as viewed from the outside (side to which the composite cable is connected) of the airtight part, of the hermetic connector shown in FIG. 3.

FIG. 4 is a perspective view, as viewed from the inside of the airtight part 52, of the hermetic connector 522. FIG. 5 is a view, as viewed from the outside (side to which the composite cable 6 is connected) of the airtight part 52, of the hermetic connector 522.

The hermetic connector 522, being a member equivalent to a wire connection device (first connector) according to an embodiment of the present disclosure, is mounted on the base-end side (side to which the photoelectric composite module 9 is connected) of the casing 521 as shown in FIG. 3.

This hermetic connector 522 is a round connector and includes a second outer frame 522A, a plate body 522B and multiple male contacts 522C as shown in FIGS. 3 to 5.

The second outer frame 522A is made of a metal material and has a circular cylindrical shape. Note that the shape of the second outer frame 522A is not limited to a circular cylindrical shape but may be any tubular shape. Specifically, the second outer frame 522A may be a tubular body having another cross-sectional shape such as an ellipse, a quadrangle and a polygon.

The plate body 522B is made of a metal material and has a disc shape. The plate body 522B closes the inside of the second outer frame 522A.

As shown in FIG. 5, multiple openings 522B1 through which the multiple male contacts 522C are respectively inserted are formed in this plate body 522B.

Each of these multiple openings 522B1 has a round shape in a plan view. As shown in FIG. 5, with the multiple male contacts 522C inserted through the multiple openings 522B1, the multiple openings 522B1 are sealed by multiple insulating members 522B2 made of an insulating material (glass material in this embodiment) and each having a round shape, respectively.

Each of the multiple male contacts 522C has a columnar shape. The multiple male contacts 522C are fitted to the plate body 522B in the state where the male contacts 522C are respectively inserted through the multiple openings 522B1 and insulated from one another by the multiple insulating members 522B2.

Hereinafter, among the multiple male contacts 522C, the male contacts 522C provided in a first area Ar1 will be described as first male contacts 522D while the male contacts 522C provided in two second areas Ar2 will be described as second male contacts 522E. In FIGS. 4 and 5, the first area Ar1 is indicated by the dashed line and the second areas Ar2 are indicated by the two-dot chain line.

Here, the first area Ar1 is a band-shaped area in the second outer frame 522A when viewed from the direction along a central axis Ax of the second outer frame 522A. Specifically, the band-shaped area includes the central axis Ax and extends in a first direction (right-left direction in FIGS. 4 and 5) orthogonal to the central axis Ax. Meanwhile, the two second areas Ar2 are areas other than the first area Ar1 in the second outer frame 522A. Each of the second areas Ar2 extends in the first direction to be parallel to the first area Ar1.

Each of the multiple first male contacts 522D is a member equivalent to a contact according to an embodiment of the present disclosure. In the first area Ar1, the multiple first male contacts 522D are arranged in two rows which are side by side in the up-down direction in FIG. 4 so as to constitute part of an equilateral triangular lattice where the interval of mutually adjacent lattice points is fixed (so that the multiple first male contacts 522D are respectively arranged at lattice points constituting part of the equilateral triangular lattice).

More specifically, the multiple (six in this embodiment) first male contacts 522D arranged side by side in the first row, which is the upper one, are arranged side by side at a first pitch P1 (FIGS. 4 and 5). Similarly to the six first male contacts 522D arranged side by side in the first row, the multiple (five in this embodiment) first male contacts 522D arranged side by side in the second row, which is the lower one, are arranged side by side at the first pitch P1, too. In addition, each first male contact 522D in the second row is arranged at a center position between the two first male contacts 522D that are arranged side by side in the first row and that are adjacent to this first male contact 522D in the second row, when viewed from the upper side of FIGS. 4 and 5.

The multiple first male contacts 522D as described above are contacts used for differential transmission. Hereinafter, among the multiple first male contacts 522D, the first male contacts 522D to which differential signals (+) are allocated will be described as male-side first differential contacts 522F (FIG. 5). Meanwhile, among the multiple first male contacts 522D, the first male contacts 522D to which differential signals (−) are allocated will be described as male-side second differential contacts 522G (FIG. 5). Furthermore, among the multiple first male contacts 522D, the first male contacts 522D to which ground is allocated will be described as male-side ground contacts 522H (FIG. 5).

Note that the arrangement (array) of the male-side first differential contacts 522F, the male-side second differential contacts 522G and the male-side ground contacts 522H is similar to that of female-side first differential contacts 916, female-side second differential contacts 917 and female-side ground contacts 918, which constitute multiple first female contacts 914. This arrangement will be described later.

Here, the openings 522B1 are formed so that an opening area size (diameter) of each of the openings 522B1 through which the male-side first and second differential contacts 522F and 522G are inserted can be different from that of each of the openings 522B1 through which the male-side ground contacts 522H are inserted, as shown in FIG. 5. In accordance with the corresponding openings 522B1, the insulating members 522B2 are also formed in different sizes.

Specifically, the openings 522B1 through which the male-side first and second differential contacts 522F and 522G are inserted are formed in the same opening area size (diameter). Meanwhile, the openings 522B1 through which the male-side ground contacts 522H are inserted are formed in a smaller opening area size (diameter) than the openings 522B1 through which the male-side first and second differential contacts 522F and 522G are inserted.

Note that the openings 522B1 through which the multiple second male contacts 522E are inserted are formed in the same opening area size (diameter) as the openings 522B1 through which the male-side ground contacts 522H are inserted, as shown in FIG. 5.

In each of the second areas Ar2, the multiple second male contacts 522E are arranged in two rows which are side by side in the up-down direction in FIG. 4.

More specifically, in the lower one of the second areas Ar2 in FIG. 4, the multiple second male contacts 522E arranged side by side in the first row, which is the upper one, are arranged side by side at a second pitch P2 (FIG. 4), which is smaller than the first pitch P1. Similarly to the multiple second male contacts 522E arranged side by side in the first row, the multiple second male contacts 522E arranged side by side in the second row, which is the lower one, are arranged side by side at the second pitch P2, too. In addition, each second male contact 522E in the second row is arranged at a center position between the two second male contacts 522E that are arranged side by side in the first row and that are adjacent to this second male contact 522E in the second row, when viewed from the upper side of FIG. 4.

The multiple second male contacts 522E arranged in the upper one of the second areas Ar2 in FIG. 4 are arranged symmetrically to the multiple second male contacts 522E arranged in the lower one of the second areas Ar2 with respect to a plane passing through the central axis Ax and being parallel to the side-by-side arrangement direction of the second male contacts 522E.

As shown in FIG. 4, an airtight-part side printed circuit board 524, which relays communication between (is electrically connected between) the multiple male contacts 522C and the image sensor 523, is mounted on the hermetic connector 522 at the side inside the airtight part 52.

The airtight-part side printed circuit board 524 relays, to the multiple first male contacts 522D, imaging signals (multiple pairs of differential signals (+) and differential signals (−)) outputted by the image sensor 523. In addition, the airtight-part side printed circuit board 524 relays, to the image sensor 523, control signals and the like (electrical signals) outputted by the controller 8 through the composite cable 6, the photoelectric composite module 9 and the multiple second male contacts 522E.

[Configuration of Photoelectric Composite Module]

Figure 7:
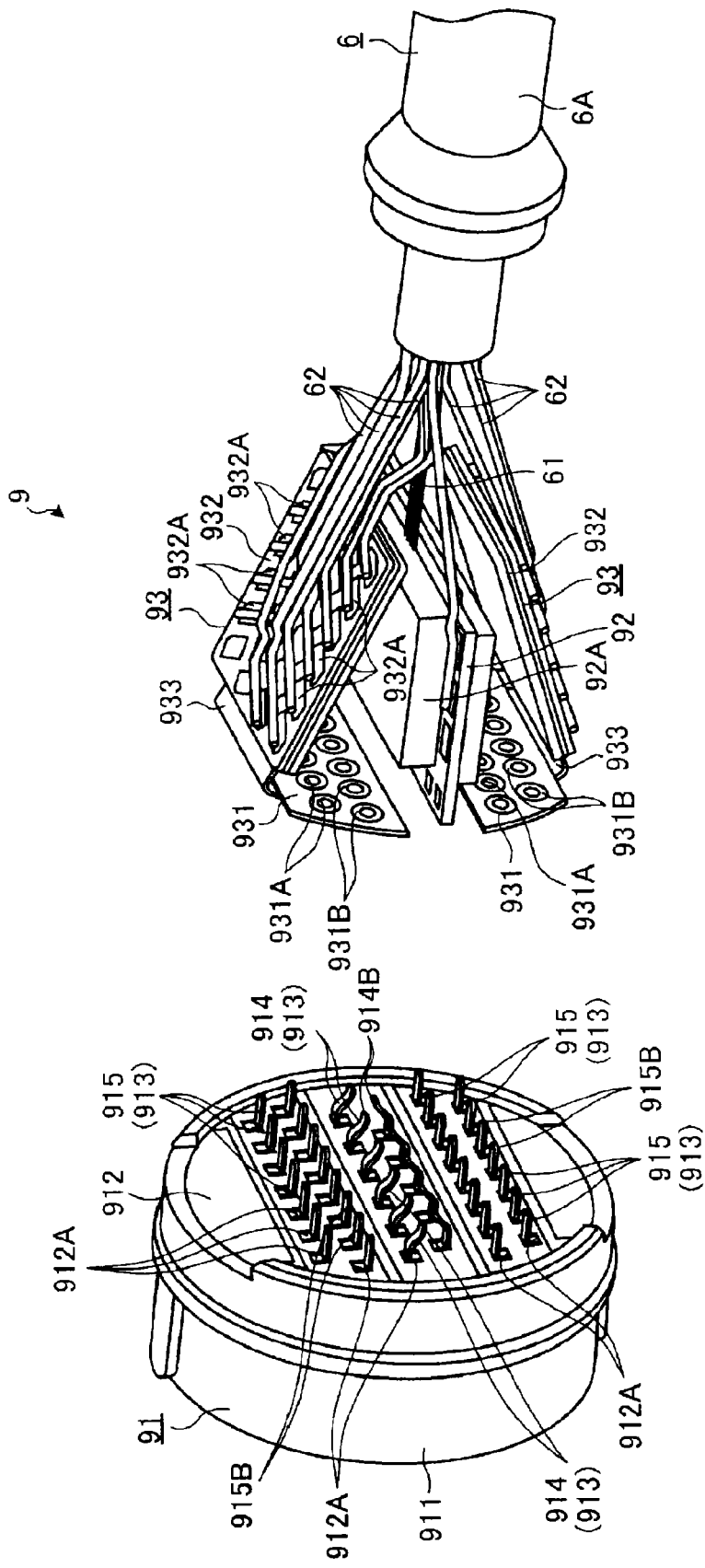
FIG. 7 is an exploded perspective view, as viewed from the base-end side (side to which the composite cable is connected), of the internal structure of the photoelectric composite module shown in FIG. 6.

FIG. 6 is a perspective view, as viewed from the front-end side (side to which the airtight part 52 is connected), of the photoelectric composite module 9. FIG. 7 is an exploded perspective view, as viewed from the base-end side (side to which the composite cable 6 is connected), of the internal structure of the photoelectric composite module 9.

The photoelectric composite module 9 is mechanically and electrically connected to the hermetic connector 522. The photoelectric composite module 9 converts imaging signals (multiple pairs of differential signals (+) and differential signals (−)) outputted by the image sensor 523 into optical signals, and then outputs the optical signals to the composite cable 6 (multiple optical fibers 61). In addition, the photoelectric composite module 9 relays, to the hermetic connector 522 (image sensor 523), control signals and the like (electrical signals) outputted by the controller 8 through the multiple electrical signal cables 62.

As shown in FIGS. 6 and 7, the photoelectric composite module 9 includes a receptacle 91, a first printed circuit board 92 (FIG. 7), two second printed circuit boards 93 (FIG. 7) and a covering member 94 (FIG. 6) which has a tubular shape and which covers the base-end side (side opposite to the side to which the hermetic connector 522 is connected) of the receptacle 91.

[Configuration of Receptacle]

Figure 8:
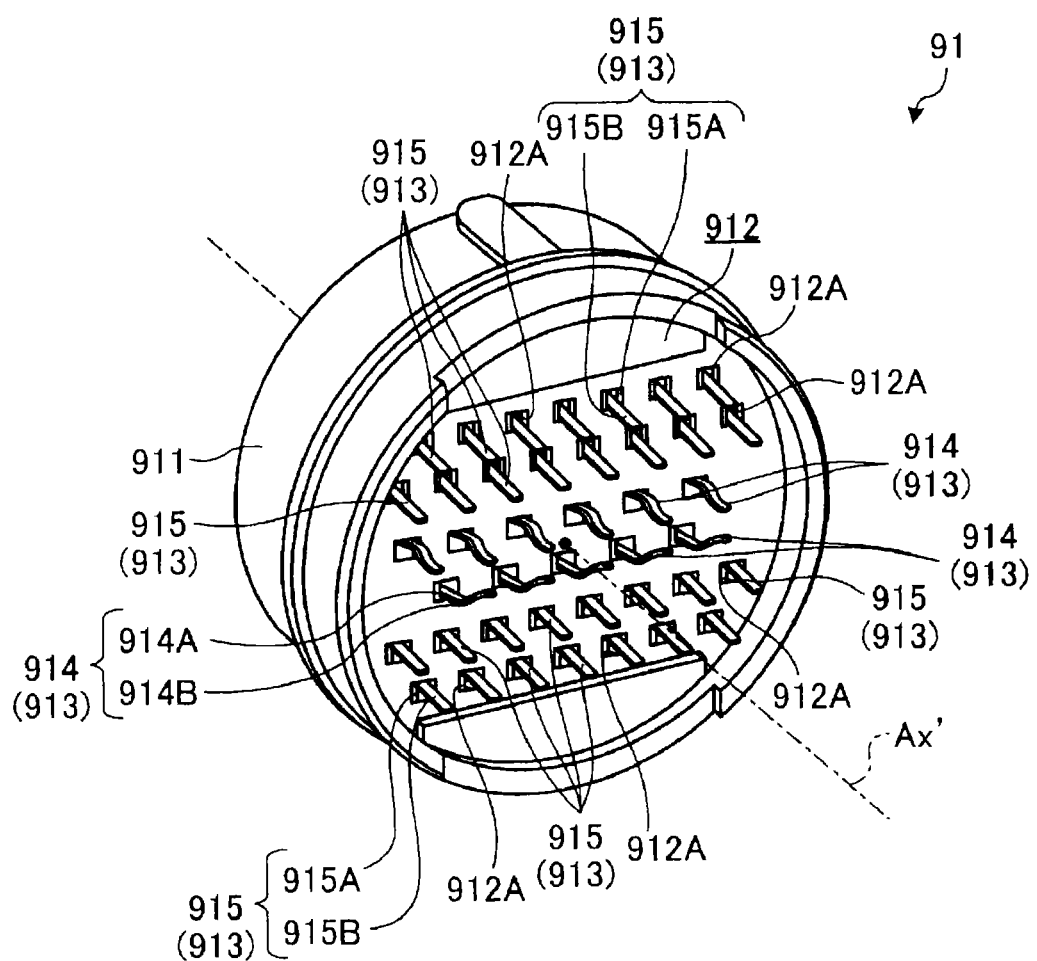
FIG. 8 is a perspective view, as viewed from the base-end side (side where first and second printed circuit boards are arranged), of the receptacle shown in FIGS. 6 and 7.

FIG. 8 is a perspective view, as viewed from the base-end side (side where the first and second printed circuit boards 92 and 93 are arranged), of the receptacle 91.

The receptacle 91, being a member equivalent to the wire connection device (second connector) according to an embodiment of the present disclosure, is a round connector mechanically and electrically connected to the hermetic connector 522, and is provided at the front end of the photoelectric composite module 9.

As shown in FIG. 8, the receptacle 91 includes a first outer frame 911, an insulator 912 and multiple female contacts 913.

The first outer frame 911 is made of a metal material and has a circular cylindrical shape. Note that the shape of the first outer frame 911 is not limited to a circular cylindrical shape but may be any tubular shape. Specifically, the first outer frame 911 may be a tubular body having another cross-sectional shape such as an ellipse, a quadrangle and a polygon.

The insulator 912 is made of an insulating material and closes the inside of the first outer frame 911.

As shown in FIGS. 6 to 8, in the insulator 912, there are formed multiple insertion holes 912A into which the multiple male contacts 522C of the hermetic connector 522 can be inserted when the hermetic connector 522 and the receptacle 91 are connected.

Each of the multiple insertion holes 912A is formed in a stepped shape as viewed from the direction along a central axis Ax' of the first outer frame 911 (FIG. 8). Specifically, in a cross sectional view, the insertion hole 912A has a round shape corresponding to the shape (columnar shape) of the male contact 522C at the front-end side (side to which the hermetic connector 522 is connected) of the receptacle 91, and, at the base-end side of the receptacle 91, has a rectangular shape surrounding this front-end side portion.

[Configuration of Female Contact]

As shown in FIG. 8, the multiple female contacts 913 are respectively provided in the multiple insertion holes 912A at the base-end side. The multiple female contacts 913 are electrically connected to the multiple male contacts 522C when the multiple male contacts 522C of the hermetic connector 522 are inserted into the multiple insertion holes 912A, respectively.

Figure 9:
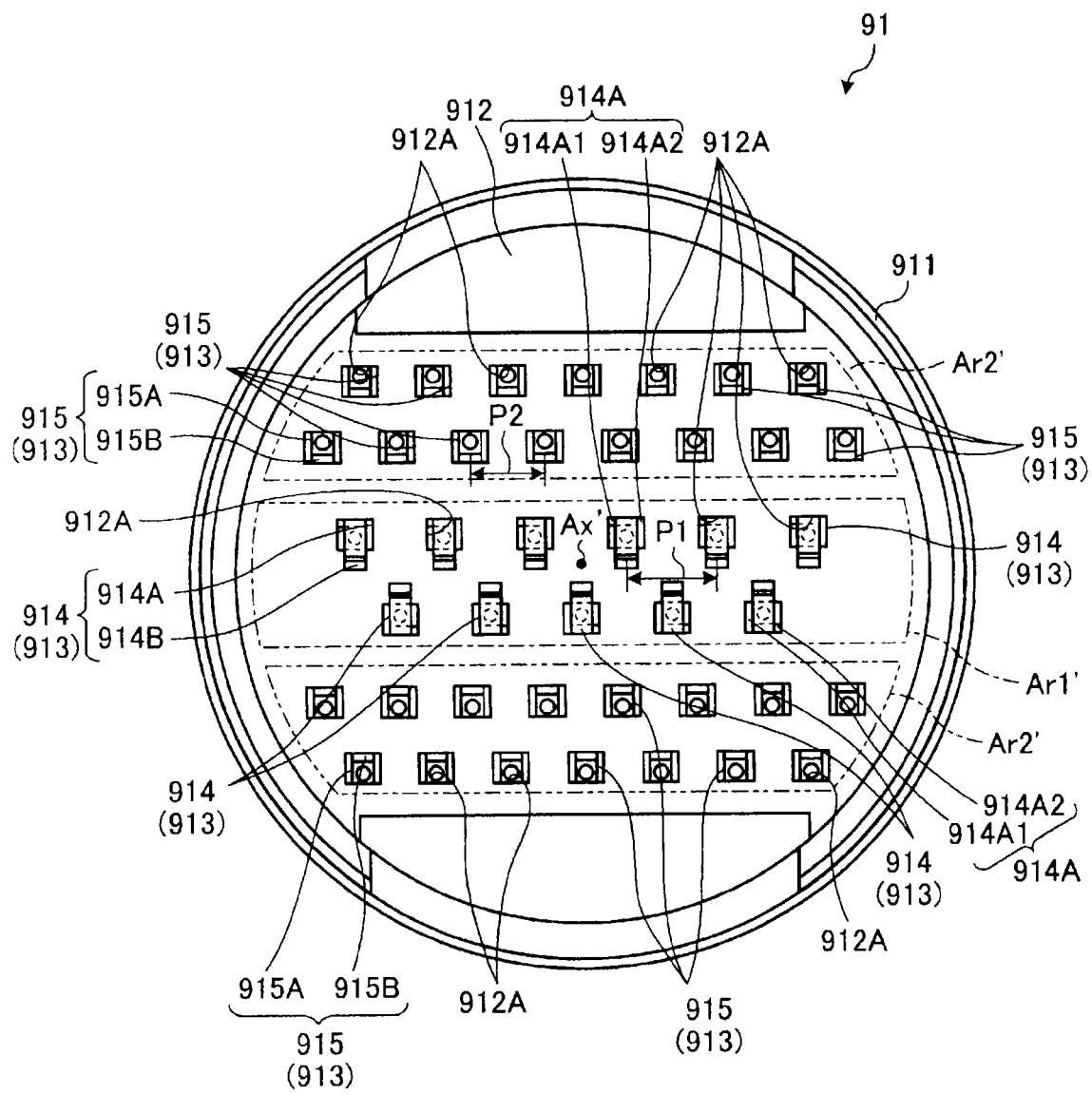
FIG. 9 shows an array state of multiple female contacts shown in FIG. 8.

FIG. 9 shows an array state of the multiple female contacts 913.

Hereinafter, among the multiple female contacts 913, the female contacts 913 provided in a first area Ar1' will be described as first female contacts 914 while the female contacts 913 provided in two second areas Ar2' will be described as second female contacts 915. In FIG. 9, the first area Ar1' is indicated by the dashed line and the second areas Ar2' are indicated by the two-dot chain line.

Here, the first area Ar1 facing the first area Ar1 shown in FIGS. 4 and 5, is a band-shaped area in the first outer frame 911 when viewed from the direction along the central axis Ax' (FIG. 9) of the first outer frame 911. Specifically, the band-shaped area includes the central axis Ax' and extends in a first direction (right-left direction in FIG. 9) orthogonal to the central axis Ax'. In other words, the first area Ar1' is a radially extending band-shaped area including the central axis Ax' when viewed from the direction along the central axis Ax'. Meanwhile, the two second areas Ar2', facing the second areas Ar2 shown in FIG. 4, are areas other than the first area Ar1 in the first outer frame 911. Each of the second areas Ar2' extends in the first direction to be parallel to the first area Ar1'.

[Configuration of First Female Contact]

The multiple first female contacts 914, each of which is a member equivalent to a contact according to an embodiment of the present disclosure, are arrayed similarly to the multiple first male contacts 522D. Specifically, in the first area Ar1', the multiple first female contacts 914 are arranged in two rows (six in the first row, five in the second row) side by side in the up-down direction in FIG. 9 so as to constitute part of an equilateral triangular lattice where the interval of mutually adjacent lattice points is fixed (so that the multiple first female contacts 914 (centroid positions of first contact portions 914A described later) are respectively arranged at lattice points constituting part of the equilateral triangular lattice).

The multiple first female contacts 914 have the same shape. Hereinafter, the shape of one of the first female contacts 914 will be described.

As shown in FIGS. 8 and 9, the first female contact 914 includes the first contact portion 914A and a first pin-shaped portion 914B.

The first contact portion 914A, provided to the inside of the insertion hole 912A, is formed in a substantially L shape when viewed from the direction along the central axis Ax' so as to extend along the central axis Ax'.

Specifically, the first contact portion 914A includes a first sidewall portion 914A1 and a second sidewall portion 914A2, as shown in FIG. 9. The first sidewall portion 914A1 has a plate shape and extends in the side-by-side arrangement direction of the first female contacts, when viewed from the direction along the central axis Ax'. The second sidewall portion 914A2 has a plate shape and extends orthogonally to the first sidewall portion 914A1.

When the male contacts 522C are inserted into the insertion holes 912A, the inner sides of each first sidewall portion 914A1 and each second sidewall portion 914A2 (inner side of the L shape) abut the outer periphery of the corresponding male contact 522C, so that the first contact portion 914A is electrically connected to the male contact 522C.

As shown in FIG. 8, the first pin-shaped portion 914B protrudes while curving from the first sidewall portion 914A1 toward the base-end side (side where the first and second printed circuit boards 92 and 93 are arranged) of the receptacle 91, and is formed elastically deformable in a leaf spring shape.

Figure 10:
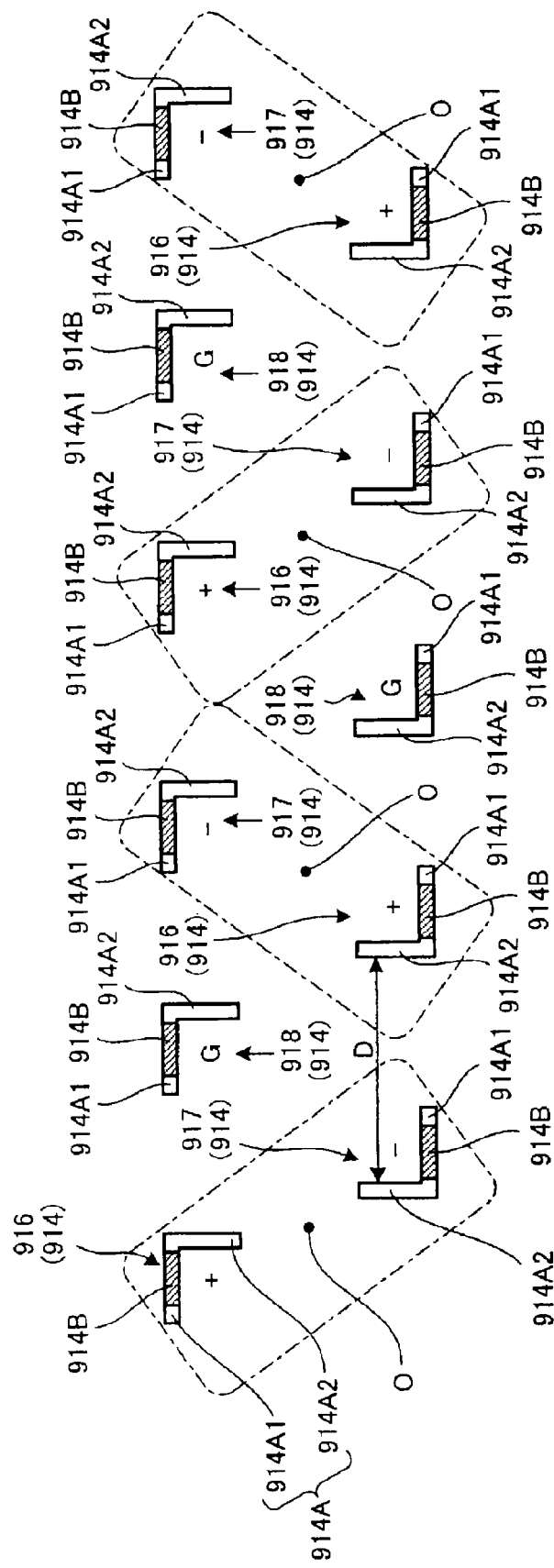
FIG. 10 is a diagram for illustrating the arrangement of the multiple first female contacts shown in FIGS. 8 and 9, and the allocation of signals and ground to the multiple first female contacts.

FIG. 10 is a diagram for illustrating the arrangement of the multiple first female contacts 914, and the allocation of signals and ground to the multiple first female contacts 914. Specifically, FIG. 10 is an enlarged view of the first area Ar1' shown in FIG. 9. Note that, for convenience of explanation, FIG. 10 shows only the first contact portions 914A of the multiple first female contacts 914 (the first pin-shaped portions 914B are cut away in FIG. 10). The letters of "+", "−" and "G" added inside the L shapes of the first female contacts 914 respectively indicate allocation of a differential signal (+), a differential signal (−) and ground. In addition, each pair of the first female contacts 914 to which a pair of a differential signal (+) and a differential signal (−) is allocated is surrounded by the dashed line.

In the first area Ar1', each of the six first female contacts 914 arranged side by side in the first row, which is the upper one, is arranged so that the first sidewall portion 914A1 can be positioned in the upper inside of the insertion hole 912A in FIGS. 9 and 10. Furthermore, the six first female contacts 914 arranged side by side in the first row are arranged so that a separation distance D (FIG. 10) between each two second sidewall portions 914A2 mutually adjacent in the side-by-side arrangement direction can be fixed. More specifically, each of the six first female contacts 914 arranged side by side in the first row is arranged so that the second sidewall portion 914A2 can be positioned on the right side (the side to the right in FIGS. 9 and 10) of the first sidewall portion 914A1.

Meanwhile, each of the five first female contacts 914 arranged side by side in the second row, which is the lower one, is arranged so that the first sidewall portion 914A1 can be positioned in the lower inside of the insertion hole 912A. Furthermore, the five first female contacts 914 arranged side by side in the second row are arranged similarly to the first row so that the separation distance D between each two second sidewall portions 914A2 mutually adjacent in the side-by-side arrangement direction can be fixed. More specifically, each of the five first female contacts 914 arranged side by side in the second row is arranged so that the second sidewall portion 914A2 can be positioned on the left side (the side to the left in FIGS. 9 and 10) of the first sidewall portion 914A1.

To each of the multiple first female contacts 914 arranged as described above, either of a differential signal (+), a differential signal (−) and ground are allocated, as described later.

Hereinafter, among the multiple first female contacts 914, the first female contacts 914 to which differential signals (+) are allocated will be described as female-side first differential contacts 916 (FIG. 10). Among the multiple first female contacts 914, the first female contacts 914 to which differential signals (−) are allocated will be described as female-side second differential contacts 917 (FIG. 10). Among the multiple first female contacts 914, the first female contacts 914 to which ground is allocated will be described as female-side ground contacts 918 (FIG. 10).

To the multiple first female contacts 914, differential signals (+), differential signals (−) and ground are allocated so that the female-side first and second differential contacts 916 and 917 of each pair, which are surrounded by the dashed line in FIG. 10, can be adjacent to each other and so that the number of the female-side ground contacts 918 adjacent to the female-side first differential contact 916 of each pair can be equal to the number of the female-side ground contacts 918 adjacent to the female-side second differential contact 917 of the pair.

Specifically, in FIG. 10, the female-side ground contacts 918 are the first female contacts 914 at the second and fifth positions from the left in the first row, which is the upper one, and the first female contact 914 at the third position from the left in the second row, which is the lower one.

In addition, in FIG. 10, as to the pair of female-side first and second differential contacts 916 and 917 arranged leftmost, the female-side first differential contact 916 is at the leftmost position in the first row, which is the upper one, and the female-side second differential contact 917 is at the leftmost position in the second row, which is the lower one. Thus, each of the female-side first and second differential contacts 916 and 917 is adjacent to just one female-side ground contact 918, that is, the female-side ground contact 918 at the second position from the left in the first row, which is the upper one, in FIG. 10.

In addition, in FIG. 10, as to the pair of female-side first and second differential contacts 916 and 917 arranged at the second position from the left, the female-side first differential contact 916 is at the second position from the left in the second row, which is the lower one, and the female-side second differential contact 917 is at the third position from the left in the first row, which is the upper one. Thus, each of the female-side first and second differential contacts 916 and 917 is adjacent to two female-side ground contacts 918, that is, the female-side ground contact 918 at the second position from the left in the first row, which is the upper one, and the female-side ground contact 918 at the third position from the left in the second row, which is the lower one, in FIG. 10.

In addition, in FIG. 10, as to the pair of female-side first and second differential contacts 916 and 917 arranged at the third position from the left, the female-side first differential contact 916 is at the fourth position from the left in the first row, which is the upper one, and the female-side second differential contact 917 is at the fourth position from the left in the second row, which is the lower one. Thus, each of the female-side first and second differential contacts 916 and 917 is adjacent to two female-side ground contacts 918, that is, the female-side ground contact 918 at the third position from the left in the second row, which is the lower one, and the female-side ground contact 918 at the fifth position from the left in the first row, which is the upper one, in FIG. 10.

In addition, in FIG. 10, as to the pair of female-side first and second differential contacts 916 and 917 arranged rightmost, the female-side first differential contact 916 is at the rightmost position in the second row, which is the lower one, and the female-side second differential contact 917 is at the rightmost position in the first row, which is the upper one. Thus, each of the female-side first and second differential contacts 916 and 917 is adjacent to just one female-side ground contact 918, that is, the female-side ground contact 918 at the fifth position from the left in the first row, which is the upper one, in FIG. 10.

In other words, as to each of the multiple ("four" in this embodiment) pairs of female-side first and second differential contacts 916 and 917, one of the differential contacts is arranged in the first row while the other one of the differential contacts is arranged in the second row.

With the arrangement, the four pairs of female-side first and second differential contacts 916 and 917 exhibit a substantially W shape as shown in FIG. 10. In addition, the female-side first and second differential contacts 916 and 917 of each of the four pairs are arranged symmetrically with respect to the point O (FIG. 10) positioned at the center between the female-side first and second differential contacts 916 and 917 of the pair.

Note that the arrangement of the multiple first male contacts 522D (male-side first and second differential contacts 522F and 522G and ground contacts 522H) is similar to that of the multiple first female contacts 914.

[Configuration of Second Female Contact]

The multiple second female contacts 915 are arranged similarly to the multiple second male contacts 522E. In other words, in each of the second areas Ar2', the multiple second female contacts 915 are arranged in two rows which are side by side in the up-down direction in FIG. 9. In addition, the multiple second female contacts 915 are arranged side by side at the second pitch P2.

The multiple second female contacts 915 have the same shape. Hereinafter, the shape of one of the second female contacts 915 will be described.

As shown in FIGS. 8 and 9, the second female contact 915 includes a main contact body 915A and a second pin-shaped portion 915B.

The main contact body 915A, provided to the inside of the insertion hole 912A, is formed in a substantially U shape when viewed from the direction along the central axis Ax' so as to extend along the central axis Ax'. When the male contacts 522C are inserted into the insertion holes 912A (see FIG. 6), the inner periphery of each U shape abuts the outer periphery of the corresponding male contact 522C, so that the main contact body 915A is electrically connected to the male contact 522C.

The second pin-shaped portion 915B protrudes linearly along the central axis Ax' from a base-end portion of the U shape of the main contact body 915A toward the base-end side of the receptacle 91.

In addition, in FIG. 9, each of the multiple second female contacts 915 arranged in the upper one of the second areas Ar2' is provided to the corresponding insertion hole 912A so that the opening of the U shape of the main contact body 915A can be directed upward. Meanwhile, each of the multiple second female contacts 915 arranged in the lower one of the second areas Ar2' is provided to the corresponding insertion hole 912A so that the opening of the U shape of the main contact body 915A can be directed downward.

[Configuration of First Printed Circuit Board]

The first printed circuit board 92 is formed of a rigid substrate on which a photoelectric conversion element 92A for converting electrical signals into optical signals is mounted. The first printed circuit board 92 is electrically connected to the multiple first female contacts 914 of the receptacle 91, and relays, to the photoelectric conversion element 92A, imaging signals (differential signals (+) and differential signals (−)) outputted by the image sensor 523 through the airtight-part side printed circuit board 524, the multiple first male contacts 522D and the multiple first female contacts 914.

Here, as shown in FIG. 7, the multiple optical fibers 61 are connected to the photoelectric conversion element 92A. In other words, the photoelectric conversion element 92A converts imaging signals (differential signals (+) and differential signals (−)) into optical signals, and then outputs the optical signals to the multiple optical fibers 61.

As shown in FIG. 7, the first printed circuit board 92 is arranged along the central axis Ax' to the base-end side of the receptacle 91.

Specifically, the first printed circuit board 92 is fitted to the receptacle 91 as described below.

The first printed circuit board 92 is inserted between the first row, which is the upper one, of the multiple first female contacts 914 (first pin-shaped portions 914B) and the second row, which is the lower one, of the multiple first female contacts 914 (first pin-shaped portions 914B), in FIG. 7. In this state, the multiple first pin-shaped portions 914B in the first and second rows hold the first printed circuit board 92 while elastically deformed by the pressing of the first printed circuit board 92. In addition, the multiple first pin-shaped portions 914B in the first and second rows are electrically connected to lands (not shown) formed on the front and back surfaces of the first printed circuit board 92. The first pin-shaped portions 914B are respectively soldered to the lands in the state, and thereby the first printed circuit board 92 is fitted to the receptacle 91.

[Configuration of Second Printed Circuit Board]

The two second printed circuit boards 93 are each formed of a flexible substrate, and relay, to the multiple second female contacts 915, control signals and the like (electrical signals) outputted by the controller 8 through the multiple electrical signal cables 62. The control signals and the like (electrical signals) relayed to the multiple second female contacts 915 are outputted to the image sensor 523 through the multiple second male contacts 522E and the airtight-part side printed circuit board 524.

These two second printed circuit boards 93 have the same configuration. Hereinafter, one of the second printed circuit boards 93 will be described.

As shown in FIG. 7, the second printed circuit board 93 includes a first contact part 931, a second contact part 932 and an installation part 933, installed between the first and second contact parts 931 and 932.

The first contact part 931 has a shape corresponding to one of the second areas Ar2'. Additionally, in the first contact part 931, there are formed multiple holes 931A (FIG. 7) respectively corresponding to the multiple second female contacts 915 (second pin-shaped portions 915B) arranged in the second area Ar2'.

The first contact part 931 is fitted to the receptacle 91, by putting the first contact part 931 on the base-end side end surface of the insulator 912 with the second female contacts 915 inserted through the respective holes 931A, and then by soldering the second pin-shaped portions 915B to lands 931B (FIG. 7) provided on the peripheries of the holes 931A, respectively.

The second contact part 93 is arranged at a position overlapping the first printed circuit board 92, in FIG. 7, by bending the installation part 933 with respect to the first contact part 931 fitted to the receptacle 91, as shown in FIG. 7.

As shown in FIG. 7, on a surface of the second contact part 932, there is formed multiple lands 932A each having a substantially rectangular shape. The second contact part 932 is electrically connected to the multiple electrical signal cables 62 by soldering the multiple electrical signal cables 62 to the multiple land 932A.

In the receptacle 91 according to this embodiment, the multiple first female contacts 914 are arranged side by side in two rows when viewed from the direction along the central axis Ax' of the first outer frame 911. Consequently, an increase in width dimension in the side-by-side arrangement direction can be avoided as compared to the configuration in which the multiple first female contacts 914 are arranged side by side in a row.

Furthermore, the multiple first female contacts 914 are arranged so that the female-side first and second differential contacts 916 and 917 of each pair can be adjacent to each other and so that the number of the female-side ground contacts 918 adjacent to the female-side first differential contact 916 of each pair can be equal to the number of the female-side ground contacts 918 adjacent to the female-side second differential contact 917 of the pair. Thus, the number of so-called ground guards for each differential signal can be fixed, and consequently signal deterioration can be prevented.

Accordingly, the receptacle 91 according to this embodiment has an effect of preventing signal deterioration while achieving downsizing. Note that the hermetic connector 522 also has a similar effect.

In addition, in the receptacle 91 according to this embodiment, the multiple first female contacts 914 are arranged so as to constitute part of an equilateral triangular lattice when viewed from the direction along the central axis Ax' of the first outer frame 911.

Accordingly, the distances between each female-side ground contact 918 and its adjacent pair of female-side first and second differential contacts 916 and 917 are the same as each other. Thus, the balance between differential signals of each pair with respect to ground can be secured, and consequently signal deterioration can be further prevented. Note that the hermetic connector 522 also has a similar effect.

In addition, in the receptacle 91 according to this embodiment, the four pairs of female-side first and second differential contacts 916 and 917 are arranged so as to exhibit a substantially W shape as viewed from the direction along the central axis Ax' of the first outer frame 911.

Accordingly, the number of the female-side ground contacts 918 can be relatively small (three). Thus reducing the number of the female-side ground contacts 918 enables downsizing of the receptacle 91. Note that the hermetic connector 522 also has a similar effect.

Furthermore, in the receptacle 91 according to this embodiment, each of the multiple first female contacts 914 includes the first contact portion 914A, which has the first and second sidewall portions 914A1 and 914A2 and which thus have an L shape as viewed from the direction along the central axis Ax' of the first outer frame 911. In addition, the multiple first female contacts 914 are arranged so that the separation distance D between each two second sidewall portions 914A2 mutually adjacent in the side-by-side arrangement direction can be fixed.

Accordingly, a sufficiently large distance can be secured as the separation distance D between each two second sidewall portions 914A2 mutually adjacent in the side-by-side arrangement direction. In other words, a sufficiently large distance can be secured as the separation distance D between the second sidewall portions 914A2 of the female-side first and second differential contacts 916 and 917 of different pairs (the female-side second differential contact 917 at the leftmost position and the female-side first differential contact 916 at the second position from the left, in the second row, which is the lower one, in FIG. 10, for example). This enables reduction of a coupling degree (electric field interference) between a differential signal (+) and a differential signal (−) of different pairs, thus suppressing crosstalk and thereby even further preventing signal deterioration. In addition, forming each first contact portion 914A in an L shape enables the first contact portion 914A to maintain sufficient strength.

In addition, in the receptacle 91 according to this embodiment, as to each of the four pairs of female-side first and second differential contacts 916 and 917, one of the differential contacts is arranged in the first row, which is the upper one, while the other one of the differential contacts is arranged in the second row, which is the lower one, in FIG. 10. Additionally, the one differential contact and the other differential contact are arranged symmetrically with respect to the point O positioned at the center therebetween.

Thus, the balance between differential signals of each pair with respect to the point O can be secured, and consequently signal deterioration can be further prevented.

In a hermetic connector of related art, multiple openings through which multiple male contacts are inserted are all formed in the same opening area size (diameter) in a plate body. Accordingly, insulating members respectively sealing the multiple openings are also formed in the same size.

Here, in raising the frequencies of differential signals, the opening area size (diameter) of the multiple openings has to be increased in order to secure an insulation distance between the plate body and each male contact.

Thus, in the hermetic connector of related art, the opening area size (diameter) of all the openings has to be increased so as to be compatible with the above case. This consequently increases the area size occupied by all the openings (insulating members) in the plate body, thus increasing the outer diameter size of the hermetic connector.

On the other hand, in this embodiment, the openings 522B 1 through which the male-side first and second differential contacts 522F and 522G are inserted are formed in the same opening area size (diameter) that is larger than the opening area size (diameter) of the openings 522B1 through which the male-side ground contacts 522H are inserted, in the plate body 522B. In addition, each of the insulating members 522B2 is formed in a size in accordance with the opening area size (diameter) of the corresponding one of the openings 522B1.

In other words, in this embodiment, only the minimum insulation distance that may be necessary to be compatible with the case of raising the frequencies of differential signals is secured between the plate body 522B and each of the male-side first and second differential contacts 522F and 522G. Thus, by minimizing the opening area size (diameter) of each of the openings 522B 1 through which the male-side ground contacts 522H and the second male contacts 522E are inserted as much as possible, the area size occupied by all the openings 522B1 (insulating members 522B2) in the plate body 522B is minimized as much as possible. Consequently, diameter reduction (downsizing) of the hermetic connector 522 can be achieved.

(Other Embodiments)

Heretofore, the embodiment for carrying out the present disclosure has been described, but the present disclosure should not be limited only to the embodiment.

In the embodiment, the number of the first female contacts 914 (first male contacts 522D) is not limited to the number (eleven) described in the embodiment.

Figure 11:
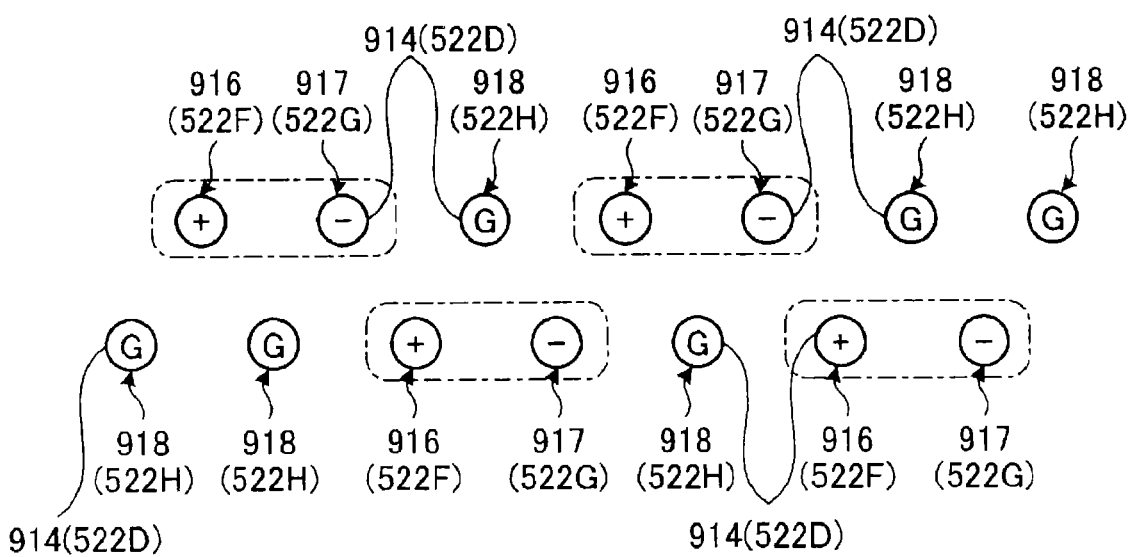
FIG. 11 shows a modification of an embodiment of the present disclosure.

FIG. 11 shows a modification of the embodiment according to the present disclosure. Specifically, FIG. 11 shows the first female contacts 914 (first male contacts 522D) as viewed from the direction along the central axis Ax' (central axis Ax) of the first outer frame 911 (second outer frame 522A).

Note that, in FIG. 11, each of the first female contacts 914 (first male contacts 522D) is indicated virtually by "O," for convenience of explanation. The letters of "+", "−" and "G" added inside the "O" respectively indicate allocation of a differential signal (+), a differential signal (−) and ground. In addition, each pair of the first female contacts 914 (first male contacts 522D) to which a pair of a differential signal (+) and a differential signal (−) is allocated is surrounded by the dashed line.

The number of the first female contacts 914 (first male contacts 522D) may be fourteen, as shown in FIG. 11. Even in such a case, the fourteen first female contacts 914 (first male contacts 522D) are preferably arranged side by side in two rows so as to constitute part of an equilateral triangular lattice, as similar to the embodiment.

Specifically, in FIG. 11, the seven first female contacts 914 (first male contacts 522D) in the first row, which is the upper one, are arranged side by side in the following order from left to right in FIG. 11: a pair of female-side first and second differential contacts 916 and 917 (male-side first and second differential contacts 522F and 522G), the female-side ground contact 918 (male-side ground contact 522H), a pair of female-side first and second differential contacts 916 and 917 (male-side first and second differential contacts 522F and 522G), the female-side ground contact 918 (male-side ground contacts 522H) and the female-side ground contacts 918 (male-side ground contact 522H). Meanwhile, the seven first female contacts 914 (first male contacts 522D) in the second row, which is the lower one, are arranged side by side in the following order from left to right in FIG. 11: the female-side ground contact 918 (male-side ground contact 522H), the female-side ground contact 918 (male-side ground contact 522H), a pair of female-side first and second differential contacts 916 and 917 (male-side first and second differential contacts 522F and 522G), the female-side ground contact 918 (male-side ground contact 522H) and a pair of female-side first and second differential contacts 916 and 917 (male-side first and second differential contacts 522F and 522G).

Thus, each of the four pairs of female-side first and second differential contacts 916 and 917 (male-side first and second differential contacts 522F and 522G) is arranged either in the first row or in the second row.

In the embodiment, there may be employed a contact portion (second contact portion 914A' and third contact portion 914A", described below, for example) having another shape different from that of the first contact portion 914A.

Figure 12:
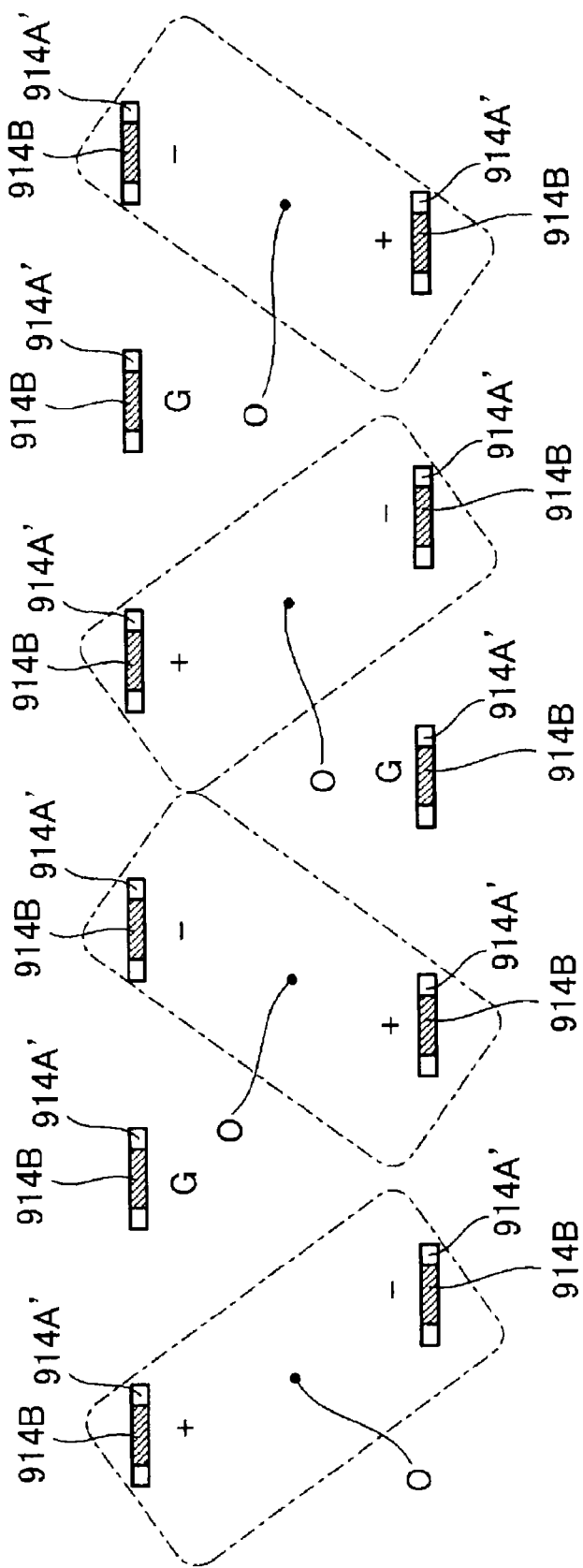
FIG. 12 shows a modification of an embodiment of the present disclosure.
Figure 13:
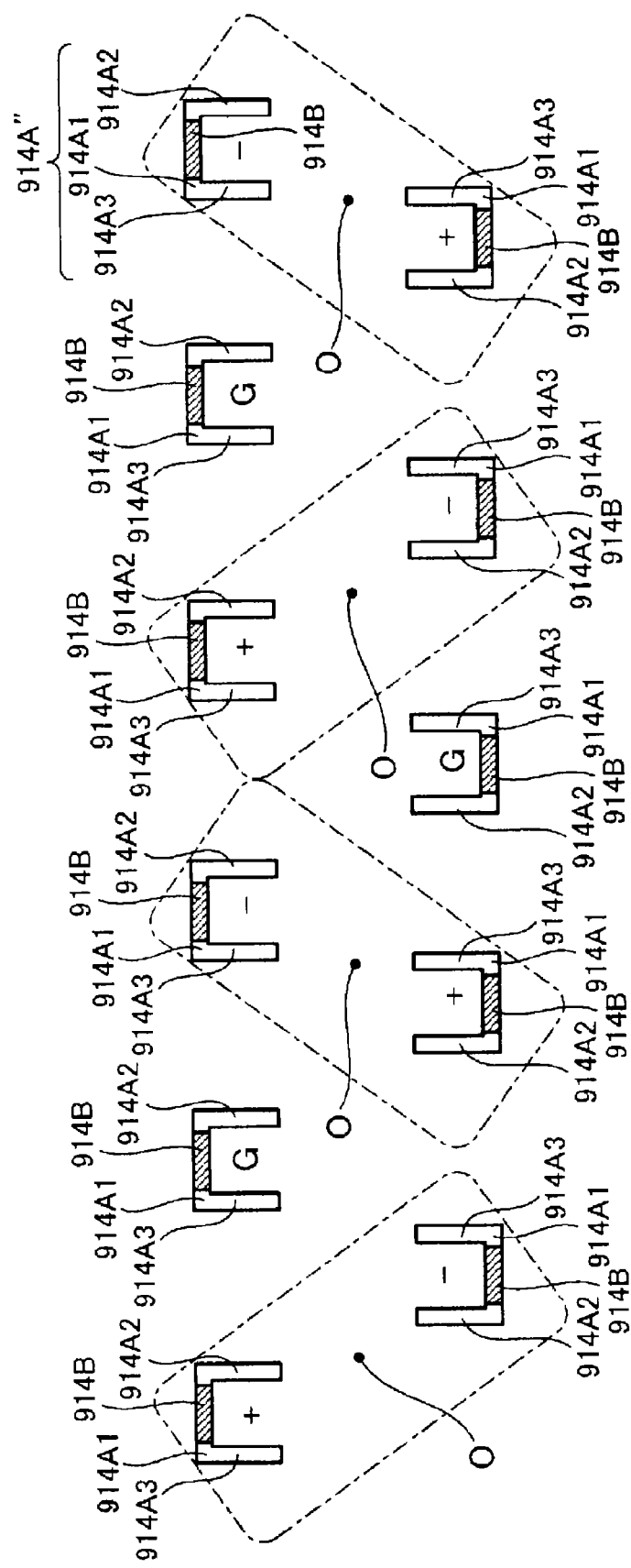
FIG. 13 shows a modification of an embodiment of the present disclosure.

FIGS. 12 and 13 show modifications of the embodiment according to the present disclosure. Specifically, each of FIGS. 12 and 13 is a diagram corresponding to FIG. 10.

For example, as shown in FIG. 12, there may be employed second contact portions 914A' each having a plate shape obtained by omitting the second sidewall portion 914A2 from the first contact portion 914A described in the embodiment. Even this configuration still enables reduction of a coupling degree (electric field interference) between a differential signal (+) and a differential signal (−) of different pairs, and thus suppresses crosstalk, thereby preventing signal deterioration.

Furthermore, as shown in FIG. 13, there may be employed third contact portions 914A" each having a U shape obtained by adding a third sidewall portion 914A3, facing the second sidewall portion 914A2, to the first contact portion 914A described in the embodiment, for example. This configuration enables the third contact portions 914A" to have an increased strength.

In the embodiment, the female-side ground contact 918 at the third position from the left in the second row, which is the lower one, FIG. 10 may be omitted. Note that this is also applicable to the hermetic connector 522 and the configurations shown in FIGS. 12 and 13. When such a configuration is employed, the number of ground guards between the female-side first and second differential contacts 916 and 917 is fixed to one. Thus, the number of the female-side ground contacts 918 can be minimized as much as possible, and thereby the receptacle 91 can be downsized.

In the embodiment, still another configuration may be employed where the receptacle 91 is omitted and where, instead, the first and second printed circuit boards 92 and 93 are connected directly, from outside of the airtight part 52, to the hermetic connector 522 mounted on the base-end side of the airtight part 52. In this case, each of the multiple male contacts 522C of the hermetic connector 522 is preferably formed in a shape similar to the first pin-shaped portions 914B of the receptacle 91 (elastically deformable in a leaf spring shape) in consideration of fitting work of the first printed circuit board 92.

In the embodiment, as the wire connection devices according to an embodiment of the present disclosure, round connectors (receptacle 91 and hermetic connector 522) are employed, but connectors each having a non-round shape may be employed. When connectors each having a non-round shape is employed, a first printed circuit board may be arranged at a position other than a center position of each connector (center position when viewed from the direction along the central axis of the connector) as long as a pitch of multiple contacts electrically connected to the first printed circuit board can be secured sufficiently large.

In the embodiment, the pitch (second pitch P2) of the multiple second female contacts 915 is set smaller than the pitch (first pitch P1) of the multiple first female contacts 914, but the pitch length is not limited thereto. The pitch of the multiple second female contacts 915 may set to larger than that of the multiple first female contacts 914.

The endoscopic device 1 according to the embodiment may be used not only in medical fields but also in industrial fields, specifically, used as an endoscopic device for observing the interior of an observation object such as a machine structure.

It should be understood by those skilled in the art that various modifications, combinations, sub-combinations and alterations may occur depending on design requirements and other factors insofar as they are within the scope of the appended claims or the equivalents thereof.

What is claimed is:

1. A wire connection device comprising:
    an outer frame that has a tubular shape; and
    a plurality of contacts that are provided in the outer frame, and that have
        a plurality of pairs of differential contacts to which a plurality of pairs of differential signals are respectively allocated, and
        a plurality of ground contacts each to which ground is allocated,
    wherein, when viewed from a direction along a central axis of the outer frame, the plurality of contacts are arranged side by side in two rows in a manner that the differential contacts of each pair can be adjacent to each other and in a manner that the number of the ground contacts adjacent to one of the differential contacts of each pair is equal to the number of the ground contacts adjacent to the other one of the differential contacts of the pair, and
    wherein the number of the plurality of ground contacts is less than the number of the plurality of pairs of differential contacts.

2. The wire connection device according to claim 1, wherein, when viewed from the direction along the central axis of the outer frame, the plurality of contacts are arranged so as to constitute part of an equilateral triangular lattice where intervals of mutually adjacent lattice points are identical.

3. The wire connection device according to claim 1, wherein the plurality of pairs of differential contacts are arranged in a manner that one of the differential contacts of each pair is arranged in a first row of the two rows while the other one of the differential contacts of the pair is arranged in a second row of the two rows.

4. The wire connection device according to claim 1, wherein the plurality of pairs of differential contacts are arranged in a manner that both the differential contacts of each pair are arranged in either of a first row and a second row of the two rows.

5. The wire connection device according to claim 1, wherein, when viewed from the direction along the central axis of the outer frame, each of the plurality of contacts is formed of a female contact including
    a first contact portion that has an L shape and that has
        a first sidewall portion extending in a side-by-side arrangement direction of either of a first row and a second row of the two rows, and
        a second sidewall portion crossing the first sidewall portion, and
    wherein the plurality of contacts are arranged in a manner that separation distances between each two of the second sidewall portions mutually adjacent in the side-by-side arrangement direction are identical.

6. The wire connection device according to claim 1, wherein each of the plurality of contacts is formed of a female contact including
    a second contact portion that has a plate shape extending in a side-by-side arrangement direction of either of a first row and a second row of the two rows.

7. The wire connection device according to claim 1, wherein, when viewed from the direction along the central axis of the outer frame, each of the plurality of contacts is formed of a female contact including
    a third contact portion that has a U shape and that has
        a base portion extending in a side-by-side arrangement direction of either of a first row and a second row of the two rows, and
        a pair of third sidewall portions erecting from the base portion and facing to each other in the side-by-side arrangement direction.

8. The wire connection device according to claim 5,
    wherein the plurality of pairs of differential contacts are arranged in a manner that one of the differential contacts of each pair is arranged in the first row while the other one of the differential contacts of the pair is arranged in the second row, and
    wherein the one differential contact and the other differential contact are arranged symmetrically with respect to a point positioned at a center between the one differential contact and the other differential contact.

9. The wire connection device according to claim 1, wherein, when viewed from the direction along the central axis of the outer frame, the plurality of contacts are arranged in a manner that the number of the ground contacts adjacent to one of the differential contacts of each pair and the number of the ground contacts adjacent to the other one of the differential contacts of the pair are set to one.

10. A camera head used in an endoscope, the camera head comprising:
    the wire connection device according to claim 1, and
    an image sensor electrically connected to the plurality of contacts.

11. The camera head according to claim 10, wherein the wire connection device is formed of two connectors mechanically and electrically connected to each other, the connectors being a first connector and a second connector.

12. An endoscopic device comprising:
    the camera head according to claim 10.

13. The wire connection device according to claim 1, wherein an insulating member associated with a ground contact is a different size from an insulating member associated with a differential contact of the plurality of pairs of differential contacts.

14. The wire connection device according to claim 1, wherein
    the outer frame includes a first area including a first plurality of contacts and a second area including a second plurality of contacts, and
    the first plurality of contacts are arranged at a different pitch than the second plurality of contacts, the pitch being a distance between a contact and an adjacent contact.

* * * * *